(12) United States Patent
Liu

(10) Patent No.: US 9,918,933 B2
(45) Date of Patent: Mar. 20, 2018

(54) MEDICINE FOR TREATMENT OR ADJUVANT TREATMENT OF ACQUIRED IMMUNODEFICIENCY SYNDROME, PREPARATION METHOD THEREFOR AND USE METHOD THEREOF

(71) Applicant: Darong Liu, Baoji (CN)

(72) Inventor: Darong Liu, Baoji (CN)

( * ) Notice: Subject to any disclaimer, the term of this patent is extended or adjusted under 35 U.S.C. 154(b) by 221 days.

(21) Appl. No.: 14/901,060

(22) PCT Filed: May 29, 2015

(86) PCT No.: PCT/CN2015/000371
§ 371 (c)(1),
(2) Date: Dec. 27, 2015

(87) PCT Pub. No.: WO2016/119089
PCT Pub. Date: Aug. 4, 2016

(65) Prior Publication Data
US 2017/0319475 A1    Nov. 9, 2017

(30) Foreign Application Priority Data
Jan. 30, 2015   (CN) .......................... 2015 1 0051136

(51) Int. Cl.
| A61K 9/00 | (2006.01) |
| A61K 9/08 | (2006.01) |
| A61K 36/236 | (2006.01) |
| A61K 36/32 | (2006.01) |
| A61K 36/489 | (2006.01) |
| A61K 36/58 | (2006.01) |
| A61K 36/00 | (2006.01) |

(52) U.S. Cl.
CPC .............. *A61K 9/0053* (2013.01); *A61K 9/08* (2013.01); *A61K 36/236* (2013.01); *A61K 36/32* (2013.01); *A61K 36/489* (2013.01); *A61K 36/58* (2013.01); *A61K 36/00* (2013.01)

(58) Field of Classification Search
None
See application file for complete search history.

(56) References Cited

U.S. PATENT DOCUMENTS

2011/0033556 A1* 2/2011 Jin .......................... A61K 36/00
                                                                    424/538

\* cited by examiner

*Primary Examiner* — Robert A Wax
*Assistant Examiner* — Thor Nielsen
(74) *Attorney, Agent, or Firm* — Gokalp Bayramoglu

(57) ABSTRACT

The present invention discloses a medicine for treatment or adjuvant treatment of acquired immunodeficiency syndrome, a preparation method thereof and use methods thereof. The medicine comprises: lightyellow sophora root, glabrous greenbrier rhizome, bark of Chinese corktree, raw sessile stemona root, alumen, coptis root, cortex dictamni, chinaberry bark and root-bark, pangolin scales, amber, eucommia bark, tree peony bark, clematis root, common cnidium fruit, Chinese angelica, licorice root, common macrocarpium fruit, barbary wolfberry fruit, medicinal indianmulberry root, cherokee rose fruit, chinaroot greenbier rhizome, akebia fruit, milkvetch root, Japanese climbing fern spore, asiatic pennywort herb, mulberry leaf and frankincense. The present invention not only provides the medicine capable of effectively treating the acquired immunodeficiency syndrome, but also enables the medicine to be capable of being used in conjunction with other medical technical means to easily achieve a more ideal treatment effect.

9 Claims, No Drawings

MEDICINE FOR TREATMENT OR ADJUVANT TREATMENT OF ACQUIRED IMMUNODEFICIENCY SYNDROME, PREPARATION METHOD THEREFOR AND USE METHOD THEREOF

TECHNICAL FIELD

The present invention relates to the technical field of molecular medicines, in particular to a medicine for treatment or adjuvant treatment of acquired immunodeficiency syndrome, a preparation method thereof and use methods thereof.

BACKGROUND

The acquired immunodeficiency syndrome (AIDS) is a communicable disease which is caused by infection of human immunodeficiency virus (HIV virus) and seriously threatens the health of people. The fatality rate of the AIDS is extremely high, but the AIDS has neither an effective vaccine for prevention nor a cure medicine at present; and moreover, the AIDS is widely spread, becomes epidemic rapidly, not only causes enormous economic losses but also seriously hinders the social development, and has become a social problem of great concern by governments around the world.

Therefore, the study of the AIDS is particularly urgent.

The present application claims the priority of Chinese Patent Application No. 201510051136.X, filed in Chinese Patent Office on Feb. 2, 2015, entitled "Medicine for Treatment or Adjuvant Treatment of Acquired Immunodeficiency Syndrome, Preparation Method thereof and Use Methods thereof", and the entire contents of which are herein incorporated by reference.

SUMMARY OF THE INVENTION

The present invention aims at providing a medicine for treatment or adjuvant treatment of acquired immunodeficiency syndrome, and also provides a preparation method and use methods for the medicine for treatment or adjuvant treatment of the acquired immunodeficiency syndrome at the same time.

The present invention discloses a medicine for treatment or adjuvant treatment of acquired immunodeficiency syndrome, and the medicine comprises: lightyellow sophora root, glabrous greenbrier rhizome, bark of Chinese corktree, raw sessile stemona root, alumen, coptis root, cortex dictamni, chinaberry bark and root-bark, pangolin scales, amber, eucommia bark, tree peony bark, clematis root, common cnidium fruit, Chinese angelica, licorice root, common macrocarpium fruit, barbary wolfberry fruit, medicinal indianmulberry root, cherokee rose fruit, chinaroot greenbier rhizome, akebia fruit, milkvetch root, Japanese climbing fern spore, asiatic pennywort herb, mulberry leaf and frankincense.

Preferably, the medicine comprises the following raw materials in parts by weight: 9-12 parts of the lightyellow sophora root, 9-12 parts of the glabrous greenbrier rhizome, 9-12 parts of the bark of Chinese corktree, 9-12 parts of the raw sessile stemona root, 9-12 parts of the alumen, 9-12 parts of the coptis root, 9-12 parts of the cortex dictamni, 9-12 parts of the chinaberry bark and root-bark, 6-8 parts of the pangolin scales, 3-4 parts of the amber, 9-12 parts of the eucommia bark, 9-12 parts of the tree peony bark, 9-12 parts of the clematis root, 5-7 parts of the common cnidium fruit, 9-12 parts of the Chinese angelica, 20-25 parts of the licorice root, 9-12 parts of the common macrocarpium fruit, 30-35 parts of the barbary wolfberry fruit, 9-12 parts of the medicinal indianmulberry root, 9-12 parts of cherokee rose fruit, 9-12 parts of chinaroot greenbier rhizome, 5-7 parts of the akebia fruit, 9-12 parts of the milkvetch root, 9-12 parts of the Japanese climbing fern spore, 9-12 parts of the asiatic pennywort herb, 9-12 parts of the mulberry leaf and 5-6 parts of the frankincense.

Preferably, the medicine further comprises 5,000-7,000 parts of liquor.

Preferably, the alcoholic strength of the liquor is 30-60% (V/V).

Preferably, the medicine further comprises an additive reagent containing thinner (X-1), 84 disinfectant, povidone iodine, dilute glutaral and peroxyacetic acid.

Preferably, the additive reagent is prepared by mixing the thinner (X-1), the 84 disinfectant, the povidone iodine, the dilute glutaral and the peroxyacetic acid together in a volume ratio of 120:0.2:0.2:0.2:0.2.

The preparation method of the medicine for treatment or adjuvant treatment of the acquired immunodeficiency syndrome comprises:

S100, preparing the additive reagent: mixing the thinner (X-1), the 84 disinfectant, the povidone iodine, the dilute glutaral and the peroxyacetic acid together to prepare the additive reagent;

S200, preparing a basic medicament: soaking the lightyellow sophora root, glabrous greenbrier rhizome, the bark of Chinese corktree, the raw sessile stemona root, the alumen, coptis root, the cortex dictamni, the chinaberry bark and root-bark, the pangolin scales, the amber, the eucommia bark, the tree peony bark, the clematis root, the common cnidium fruit, the Chinese angelica, the licorice root, the common macrocarpium fruit, the barbary wolfberry fruit, the medicinal indianmulberry root, the cherokee rose fruit, the chinaroot greenbier rhizome, the akebia fruit, milkvetch root, the Japanese climbing fern spore, the asiatic pennywort herb, the mulberry leaf and the frankincense in the liquor to prepare the basic medicament;

S300, adding the additive reagent into the basic medicament; and

S400, carrying out sealed preservation for 7-10 days.

Preferably, the thinner (X-1), the 84 disinfectant, the povidone iodine, the dilute glutaral and the peroxyacetic acid are mixed together in the volume ratio of 120:0.2:0.2:0.2:0.2 to prepare the additive reagent;

the basic medicament is prepared from the following raw materials in parts by weight: 9-12 parts of the lightyellow sophora root, 9-12 parts of the glabrous greenbrier rhizome, 9-12 parts of the bark of Chinese corktree, 9-12 parts of the raw sessile stemona root, 9-12 parts of alumen, 9-12 parts of coptis root, 9-12 parts of the cortex dictamni, 9-12 parts of the chinaberry bark and root-bark, 6-8 parts of the pangolin scales, 3-4 parts of the amber, 9-12 parts of the eucommia bark, 9-12 parts of the tree peony bark, 9-12 parts of the clematis root, 5-7 parts of the common cnidium fruit, 9-12 parts of the Chinese angelica, 20-25 parts of the licorice root, 9-12 parts of common macrocarpium fruit, 30-35 parts of the barbary wolfberry fruit, 9-12 parts of medicinal indianmulberry root, 9-12 parts of cherokee rose fruit, 9-12 parts of chinaroot greenbier rhizome, 5-7 parts of the akebia fruit, 9-12 parts of milkvetch root, 9-12 parts of Japanese climbing fern spore, 9-12 parts of asiatic pennywort herb, 9-12 parts of mulberry leaf and 5-6 parts of frankincense, which are soaked in 5,000-7,000 parts of the liquor with the alcoholic strength of 30-60% (V/V); and 0.5-0.7 part of the additive reagent is added into the basic medicament.

Preferably, the thinner (X-1), the 84 disinfectant, the povidone iodine, the dilute glutaral and the peroxyacetic acid are mixed together in the volume ratio of 120:0.2:0.2:0.2:0.2 to prepare the additive reagent;

the basic medicament is prepared from the following raw materials in parts by weight: 9-12 parts of the lightyellow sophora root, 9-12 parts of the glabrous greenbrier rhizome, 9-12 parts of bark of the Chinese corktree, 9-12 parts of the raw sessile stemona root, 9-12 parts of the alumen, 9-12 parts of the coptis root, 9-12 parts of the cortex dictamni, 9-12 parts of chinaberry bark and root-bark, 6-8 parts of the pangolin scales, 3-4 parts of the amber, 9-12 parts of the eucommia bark, 9-12 parts of the tree peony bark, 9-12 parts of the clematis root, 5-7 parts of the common cnidium fruit, 9-12 parts of the Chinese angelica, 20-25 parts of the licorice root, 9-12 parts of the common macrocarpium fruit, 30-35 parts of the barbary wolfberry fruit, 9-12 parts of medicinal indianmulberry root, 9-12 parts of the cherokee rose fruit, 9-12 parts of chinaroot greenbier rhizome, 5-7 parts of the akebia fruit, 9-12 parts of the milkvetch root, 9-12 parts of the Japanese climbing fern spore, 9-12 parts of the asiatic pennywort herb, 9-12 parts of the mulberry leaf and 5-6 parts of the frankincense, which are soaked in 5,000-7,000 parts of the liquor with the alcoholic strength of 30-60% (V/V); and 0.5-0.7 part of the additive reagent is added into the basic medicament, and then 250-300 parts of red date and 400-500 parts of hesperidium are added into the basic medicament.

The use methods of the medicine for treatment or adjuvant treatment of the acquired immunodeficiency syndrome comprise:

an oral administration method: a patient drinks the medicine directly, or takes the medicine by adding into drinking water and foods;

an external pasting method: the medicine is poured on gauze, then the gauze is pasted on a disease part, and then the gauze is covered with a plastic film by pasting and is fixed;

an air-permeable external pasting method: the medicine is poured on gauze, and then the gauze is pasted on the disease part and is fixed; and a smearing method: the disease part is smeared with wood lock medicated oil or safflower oil at first, and then is smeared with the medicine.

According to the medicine for treatment or adjuvant treatment of the acquired immunodeficiency syndrome, and the preparation method and the use methods of the medicine, at least one of the following positive effects can be achieved:

(1) The present invention provides the medicine capable of effectively treating the acquired immunodeficiency syndrome, and the medicine can achieve ideal effects of effectively inhibiting the HIV virus, protecting the immune system of a patient and improving the quality of life of the patient.

(2) The medicine provided by the present invention also can serve as an adjuvant treatment medicine, is used by matching with other medical technical means, and can achieve a more ideal treatment effect easily, so that the medicine provided by the present invention has a more extensive application scope and a greater clinical popularization value.

(3) The medicine provided by the present invention not only has an obvious effect of treating the acquired immunodeficiency syndrome but also has small toxic or side effects, thereby being beneficial for the patient to recuperate as soon as possible.

(4) The medicine provided by the present invention has a simple preparation process and a relatively low preparation cost, and is extremely convenient to use, thereby being beneficial for clinical large-scale popularization and application.

DETAIL DESCRIPTION OF THE INVENTION

The present invention will be further described in detail below through specific embodiments. It should be noted that the embodiments in the present application and the characteristics in the embodiments can be combined with one another without conflicts. The embodiments are exemplary and are only used for interpreting the present invention but not limiting the present invention. Moreover, unless clearly specified, all the materials adopted in the following embodiments can be purchased in the market, and specific experimental methods unmentioned in the embodiments are carried out according to conventional experimental methods in the technical field or can be obtained easily by those skilled in the field.

Embodiment 1

The preparation method of the medicine for treatment or adjuvant treatment of the acquired immunodeficiency syndrome comprises the following steps:

(1) Preparing an Additive Reagent:

adding 120 ml of thinner (X-1) into a small bottle of about 200 ml with a cover, then dropwise adding 0.2 ml of 84 disinfectant, 0.2 ml of povidone iodine, 0.2 ml of dilute glutaral and 0.2 ml of peroxyacetic acid in sequence, mixing uniformly, and covering the bottle cover for use;

(2) Preparing a Basic Medicament:

soaking 9 g of lightyellow sophora root, 9 g of glabrous greenbrier rhizome, 9 g of bark of Chinese corktree, 9 g of raw sessile stemona root, 9 g of alumen, 9 g of coptis root, 9 g of cortex dictamni, 9 g of chinaberry bark and root-bark, 6 g of pangolin scales, 3 g of amber, 9 g of eucommia bark, 9 g of tree peony bark, 9 g of clematis root, 5 g of common cnidium fruit, 9 g of Chinese angelica, 20 g of licorice root, 9 g of common macrocarpium fruit, 30 g of barbary wolfberry fruit, 9 g of medicinal indianmulberry root, 9 g of cherokee rose fruit, 9 g of chinaroot greenbier rhizome, 5 g of akebia fruit, 9 g of milkvetch root, 9 g of Japanese climbing fern spore, 9 g of asiatic pennywort herb, 9 g of mulberry leaf and 5 g of frankincense in 6 kg of sorghum liquor with the alcoholic strength of 30% (V/V); and (3) preparing the medicine:

adding 0.5 ml of the additive reagent prepared in the step (1) into the basic medicament prepared in the step (2), and carrying out sealed preservation for 7 days, wherein After the additive reagent is used for a plurality of times, adding the additive reagent again can be stopped according to the state of an illness.

Embodiment 2

The preparation method of the medicine for treatment or adjuvant treatment of the acquired immunodeficiency syndrome comprises the following steps:

(1) Preparing an Additive Reagent:

adding 120 ml of thinner (X-1) into a small bottle of about 200 ml with a cover, then dropwise adding 0.2 ml of 84 disinfectant, 0.2 ml of povidone iodine, 0.2 ml of dilute glutaral and 0.2 ml of peroxyacetic acid in sequence, mixing uniformly, and covering the bottle cover for use, wherein the thinner which burns without smoke and pungent smell is preferably used.

(2) Preparing a Basic Medicament:

soaking 10 g of lightyellow sophora root, 10 g of glabrous greenbrier rhizome, 10 g of bark of Chinese corktree, 10 g of raw sessile stemona root, 10 g of alumen, 10 g of coptis root, 10 g of cortex dictamni, 10 g of chinaberry bark and root-bark, 6 g of pangolin scales, 3 g of amber, 10 g of eucommia bark, 10 g of tree peony bark, 10 g of clematis root, 5 g of common cnidium fruit, 10 g of Chinese angelica, 20 g of licorice root, 10 g of common macrocarpium fruit, 30 g of barbary wolfberry fruit, 10 g of medicinal indian-mulberry root, 10 g of cherokee rose fruit, 10 g of chinaroot greenbier rhizome, 5 g of akebia fruit, 10 g of milkvetch root, 10 g of Japanese climbing fern spore, 10 g of asiatic pennywort herb, 10 g of mulberry leaf and 5 g of frankincense in 5 kg of sorghum liquor with the alcoholic strength of 60% (V/V); and (3) Preparing the Medicine:

adding 0.7 ml of the additive reagent prepared in the step (1) into the basic medicament prepared in the step (2), and carrying out sealed preservation for 9 days.

Embodiment 3

The preparation method of the medicine for treatment or adjuvant treatment of the acquired immunodeficiency syndrome comprises the following steps:

(1) Preparing an Additive Reagent:

adding 120 ml of thinner (X-1) into a small bottle of about 200 ml with a cover, then dropwise adding 0.2 ml of 84 disinfectant, 0.2 ml of povidone iodine, 0.2 ml of dilute glutaral and 0.2 ml of peroxyacetic acid in sequence, mixing uniformly, and covering the bottle cover for use;

(2) Preparing a Basic Medicament:

soaking 12 g of lightyellow sophora root, 12 g of glabrous greenbrier rhizome, 12 g of bark of Chinese corktree, 12 g of raw sessile stemona root, 12 g of alumen, 12 g of coptis root, 12 g of cortex dictamni, 12 g of chinaberry bark and root-bark, 8 g of pangolin scales, 4 g of amber, 12 g of eucommia bark, 12 g of tree peony bark, 12 g of clematis root, 7 g of common cnidium fruit, 12 g of Chinese angelica, 25 g of licorice root, 12 g of common macrocarpium fruit, 35 g of barbary wolfberry fruit, 12 g of medicinal indian-mulberry root, 12 g of cherokee rose fruit, 12 g of chinaroot greenbier rhizome, 7 g of akebia fruit, 12 g of milkvetch root, 12 g of Japanese climbing fern spore, 12 g of asiatic pennywort herb, 12 g of mulberry leaf and 6 g of frankincense in 7 kg of sorghum liquor with the alcoholic strength of 60% (V/V); and (3) Preparing the Medicine:

adding 0.7 ml of the additive reagent prepared in the step (1) into the basic medicament prepared in the step (2), and carrying out sealed preservation for 10 days.

Embodiment 4

The preparation method of the medicine for treatment or adjuvant treatment of the acquired immunodeficiency syndrome comprises the following steps:

(1) Preparing an Additive Reagent:

adding 120 ml of thinner (X-1) into a small bottle of about 200 ml with a cover, then dropwise adding 0.2 ml of 84 disinfectant, 0.2 ml of povidone iodine, 0.2 ml of dilute glutaral and 0.2 ml of peroxyacetic acid in sequence, mixing uniformly, and covering the bottle cover for use;

(2) Preparing a Basic Medicament:

soaking 10 g of lightyellow sophora root, 10 g of glabrous greenbrier rhizome, 10 g of bark of Chinese corktree, 10 g of raw sessile stemona root, 10 g of alumen, 10 g of coptis root, 10 g of cortex dictamni, 10 g of chinaberry bark and root-bark, 6 g of pangolin scales, 3 g of amber, 10 g of eucommia bark, 10 g of tree peony bark, 10 g of clematis root, 5 g of common cnidium fruit, 10 g of Chinese angelica, 20 g of licorice root, 10 g of common macrocarpium fruit, 30 g of barbary wolfberry fruit, 10 g of medicinal indian-mulberry root, 10 g of cherokee rose fruit, 10 g of chinaroot greenbier rhizome, 5 g of akebia fruit, 10 g of milkvetch root, 10 g of Japanese climbing fern spore, 10 g of asiatic pennywort herb, 10 g of mulberry leaf and 5 g of frankincense in 5 kg of sorghum liquor with the alcoholic strength of 60% (V/V); and (3) Preparing the Medicine:

adding 0.6 ml of the additive reagent prepared in the step (1) into the basic medicament prepared in the step (2), then adding 250 g of red date and 400 g of hesperidium and carrying out sealed preservation for 9 days, wherein the added red date and hesperidium improve the palatability of the medicine.

Embodiment 5

The preparation method of the medicine for treatment or adjuvant treatment of the acquired immunodeficiency syndrome comprises the following steps:

(1) Preparing an Additive Reagent:

adding 120 ml of thinner (X-1) into a small bottle of about 200 ml with a cover, then dropwise adding 0.2 ml of 84 disinfectant, 0.2 ml of povidone iodine, 0.2 ml of dilute glutaral and 0.2 ml of peroxyacetic acid in sequence, mixing uniformly, and covering the bottle cover for use;

(2) Preparing a Basic Medicament:

soaking 10 g of lightyellow sophora root, 10 g of glabrous greenbrier rhizome, 10 g of bark of Chinese corktree, 10 g of raw sessile stemona root, 10 g of alumen, 10 g of coptis root, 10 g of cortex dictamni, 10 g of chinaberry bark and root-bark, 6 g of pangolin scales, 3 g of amber, 10 g of eucommia bark, 10 g of tree peony bark, 10 g of clematis root, 5 g of common cnidium fruit, 10 g of Chinese angelica, 20 g of licorice root, 10 g of common macrocarpium fruit, 30 g of barbary wolfberry fruit, 10 g of medicinal indian-mulberry root, 10 g of cherokee rose fruit, 10 g of chinaroot greenbier rhizome, 5 g of akebia fruit, 10 g of milkvetch root, 10 g of Japanese climbing fern spore, 10 g of asiatic pennywort herb, 10 g of mulberry leaf and 5 g of frankincense in 5 kg of sorghum liquor with the alcoholic strength of 60% (V/V); and (3) Preparing the Medicine:

adding 0.7 ml of the additive reagent prepared in the step (1) into the basic medicament prepared in the step (2), then adding 300 g of red date and 500 g of hesperidium and carrying out sealed preservation for 10 days, wherein the added red date and hesperidium improve the palatability of the medicine.

Embodiment 6

An External Pasting Method of the Medicine:

A plurality of layers of clean gauze are folded according to the size of an affected part, then an appropriate amount of the medicine prepared in the embodiment 2 is poured on the gauze advisably until the entire gauze is soaked, then the gauze is pasted on the affected part and is covered with a slightly larger plastic film, and bandages, adhesive tapes or other appliances convenient for fixation are used for fixing and bandaging the gauze.

Embodiment 7

An external pasting method of the medicine:

A plurality of layers of clean gauze are folded according to the size of an affected part, a little "Hongli" wood lock medicated oil (or safflower oil or other similar medicines) is smeared or sprayed on the gauze, then an appropriate amount of the medicine prepared in the embodiment 3 is poured on the gauze advisably until the entire gauze is soaked, a little "Hongli" wood lock medicated oil (or safflower oil or other similar medicines) is uniformly smeared or sprayed on the affected part, then the gauze is pasted on the affected part and is covered with a slightly larger plastic film, and bandages, adhesive tapes or other appliances convenient for fixation are used for fixing and bandaging the gauze.

Embodiment 8

An air-permeable external pasting method of the medicine:

A plurality of layers of clean gauze are folded according to the size of an affected part, then an appropriate amount of the medicine prepared in the embodiment 3 is poured on the gauze advisably until the entire gauze is soaked, then the gauze is pasted on the affected part, and bandages, adhesive tapes or other appliances convenient for fixation are used for fixing and bandaging the gauze.

Embodiment 9

An air-permeable external pasting method of the medicine:

A plurality of layers of clean gauze are folded according to the size of an affected part, a little "Hongli" wood lock medicated oil (or safflower oil or other similar medicines) is uniformly smeared or sprayed on the gauze and the affected part, then an appropriate amount of the medicine prepared in the embodiment 1 is poured on the gauze advisably until the entire gauze is soaked, then the gauze is pasted on the affected part, and bandages, adhesive tapes or other appliances convenient for fixation are used for fixing and bandaging the gauze.

Embodiment 10

A smearing method of the medicine:

An affected part is smeared with wood lock medicated oil at first, and then an appropriate amount of the medicine prepared in the embodiment 2 is smeared on the affected part. This method is used for treating muscular pain caused by virus invasion, and the number of treatments is determined according to actual needs.

Embodiment 11

A Smearing Method of the Medicine:

An affected part is smeared with safflower oil or other similar medicines at first, and then an appropriate amount of the medicine prepared in the embodiment 3 is smeared on the affected part. This method is used for treating muscular pain caused by virus invasion, and the number of treatments is determined according to actual needs.

Certainly, the use methods of the medicine in the embodiments 6, 7, 8, 9, 10 and 11 can be combined with an oral administration method of the medicine in this embodiment.

Embodiment 12

An oral administration method of the medicine:

0.02-0.05 ml of "bromogeramine" and 0.02-0.05 ml of "ethacridine lactate solution" are added into 15 ml of the medicine prepared in the embodiment 4 for drinking 2 hours before meals. Besides, a cup of sweet tea is made for drinking before meals, and the medicine can be used by matching with medicines including ceftriaxone, erythromycin ethylsuccinate, amoxicillin capsules and the like.

It is understandable that on the basis of the embodiments of the present invention, the medicine of the present invention can be further prepared into other medically acceptable preparation forms, for example, tablets, injections, capsule granules and the like, by related technical staff, other medically acceptable medicine use methods, for example, injection and the like, can be used at the same time, and all these changes fall within the protection scope of the present invention.

Embodiment 13

Toxicity Test of the Medicine

In the process of an acute toxicity test, 20 white mice with half males and half females, weighing 20+/−3 g, are selected, the mice of an administration group are given 0.2 ml (equivalent to 500 times the clinical dosage by body weight) of the medicine prepared in the embodiment 2 daily by virtue of intragastric administration, and the mice of a blank control group are given the same amount of distilled water by virtue of intragastric administration. After administration, the mice of the administration group return to normal after being in a state of being drunk for 3 hours, and discharge medicine feces successively. All the mice are normally fed continuously for two weeks and have no death, and eating behaviors and body weight increase of the mice are not adversely effected.

In the process of a long-term toxicity test, with the reference of the above acute toxicity test, the medicine is mixed into daily foods of mice at large, medium and small dosages (equivalent to 50 times, 20 times, 5 times the clinical dosage by body weight respectively); after 6 months of feeding, blood biochemical examinations of all the mice do not show adverse reactions; liver and kidney functions and glucolipid metabolism of the mice in large, medium and small dosage administration groups, compared with a blank control group, do not have adverse effects; and pathological examinations of organs including sciatic nerves, testicles, prostates, ovaries, uteri and the like also do not show medicine-induced pathomorphological damages.

Conclusion: By the above medicine toxicity tests, the medicinal preparation provided by the present invention has no adverse effect on appearance signs, activities, feeding, and main organ tissues of animals, and blood routine examinations and blood biochemical examinations show that the medicine has no obvious adverse effect on blood systems, liver and kidney functions and glucolipid metabolism, so that the medicine provided by the present invention is relatively high in safety.

Embodiment 14

Clinical Treatment Experiments

Case 1

Zhang, diagnosed as an HIV infected person by CDC (Center for Disease Control) in 2010, was always treated by using other methods, an examination in 2011 showed the CD4 cell count was 332 and the weight was 65 kg, and Zhang started to have headache, asthenia and rotten legs from 2012. By virtue of environment improvement and sterilization, and treatment by using the medicine prepared in the embodiment 4 according to the oral administration method of the embodiment 12, and combining the use of the medicine prepared in the embodiment 2 according to the external pasting method of the embodiment 6, the body returned to normal, and the CD4 cell count was 535 by virtue of an examination in May 2013.

Case 2

Duan was diagnosed as an HIV infected person by CDC in 2006 with the CD4 cell count of 573, and started to have body itching and have no appetite in June 2006, and the CD4 cell count was 223 by virtue of an examination. By virtue of environment improvement and sterilization, and the use of the medicine prepared in the embodiment 5 according to the oral administration method of the embodiment 12, the body itching of Duan disappeared, the appetite of Duan turned for the better, the metal state of Duan gradually turned for the better, and the CD4 cell count was 425 by virtue of an examination in 2008.

Case 3

Wang felt headache, was subjected to general weakness and numbness in both legs in 2000, was diagnosed as an HIV infected person by CDC with the CD4 cell count of 455, and started to have general aching with the waist unable to straighten up due to lumbago and general weakness and looked skinny from 2012. By virtue of environment improvement and sterilization, and treatment by using the medicine prepared in the embodiment 2 according to the smearing method of the embodiment 10, the state of the illness turned for the better, the lumbago was cured, the appetite was increased, the mental state was recovered, and the cell count was 422 by virtue of an examination in May 2013.

Case 4

Ye felt extremely weak and dizzy, sweated with an ineffable unpleasant smell, had urethral obstruction and red fingers two days after a sole was punctured by an iron wire in 2009, then was examined with positive HIV and was diagnosed as an HIV infected person by CDC conclusive test with the CD4 cell count of 455, and one month of intravenous antiviral therapy was invalid. By virtue of environment improvement and sterilization and use of the medicine prepared in the embodiment 3 according to the external pasting method of the embodiment 7, body functions returned to normal, and the CD4 cell count was examined to be 415 in May 2014.

Conclusion: The above clinical treatment results further prove that the medicine provided by the present invention has an obvious effect for treatment and adjuvant treatment of the acquired immunodeficiency syndrome, and has ideal effects of effectively inhibiting the HIV virus, protecting the immune system of a patient and improving the quality of life of the patient.

The above-mentioned embodiments are just preferred embodiments of the present invention and are not used for limiting the present invention, and those skilled in the art can make various modifications and variations. Any modifications, equivalent substitutions, improvements and the like made within the spirit and the principle of the present invention shall be included in the protection scope of the present invention.

The invention claimed is:

1. A medicine for treatment or adjuvant treatment of the acquired immunodeficiency syndrome, comprising the following raw materials in parts by weight: 9-12 parts of lightyellow sophora root, 9-12 parts of glabrous greenbrier rhizome, 9-12 parts of bark of Chinese corktree, 9-12 parts of raw sessile stemona root, 9-12 parts of alumen, 9-12 parts of coptis root, 9-12 parts of cortex dictamni, 9-12 parts of chinaberry bark and root-bark, 6-8 parts of pangolin scales, 3-4 parts of anther, 9-12 parts of eucommia bark, 9-12 parts of tree peony bark, 9-12 parts of clematis root, 5-7 parts of common cnidium fruit, 9-12 parts of Chinese angelica, 20-25 parts of licorice root, 9-12 parts of common macrocarpium fruit, 30-35 parts of barbary wolfberry fruit, 9-12 parts of medicinal indianmulberry root, 9-12 parts of cherokee rose fruit, 9-12 parts of chinaroot greenbrier rhizome, 5-7 parts of akebia fruit, 9-12 parts of milkvetch root, 9-12 parts of Japanese climbing fern spore, 9-12 parts of asiatic pennywort herb, 9-12 parts of mulberry leaf and 5-6 parts of frankincense.

2. The medicine for treatment or adjuvant treatment of the acquired immunodeficiency syndrome according to claim 1, further comprising 5,000-7,000 parts of liquor.

3. The medicine for treatment or adjuvant treatment of the acquired immunodeficiency syndrome according to claim 2, wherein the alcoholic strength of the liquor is 30-60% (V/V).

4. The medicine for treatment or adjuvant treatment of the acquired immunodeficiency syndrome according to claim 1, further comprising an additive reagent containing thinner, disinfectant, povidone iodine, dilute glutaral and peroxyacetic acid.

5. The medicine for treatment or adjuvant treatment of the acquired immunodeficiency syndrome according to claim 4, wherein the additive reagent is prepared by mixing the thinner, the disinfectant, the povidone iodine, the dilute glutaral and the peroxyacetic acid together in a volume ratio of 120:0.2:0.2:0.2:0.2.

6. A preparation method of the medicine for treatment or adjuvant treatment of the acquired immunodeficiency syndrome according to claim 1, comprising:

preparing the additive reagent: mixing the thinner, the disinfectant, the povidone iodine, the dilute glutaral and the peroxyacetic acid together to prepare the additive reagent;

preparing a basic medicament: soaking the lightyellow sophora root, the glabrous greenbrier rhizome, the bark of Chinese corktree, the raw sessile stemona root, the alumen, the coptis root, the cortex dictamni, the chinaberry bark and root-bark, the pangolin scales, the amber, the eucommia bark, the tree peony bark, the clematis root, the common cnidium fruit, the Chinese angelica, the licorice root, the common macrocarpium fruit, the barbary wolfberry fruit, the medicinal indiannmulberry root, the cherokee rose fruit, the chinaroot greenbrier rhizome, the akebia fruit, the milkvetch root, the Japanese climbing fern spore, the asiatic pennywort herb, the mulberry leaf and the frankincense in the liquor to prepare the basic medicament;

adding the additive reagent into the basic medicament; and carrying out sealed preservation for 7-10 days.

7. The preparation method of the medicine for treatment or adjuvant treatment of the acquired immunodeficiency syndrome according to claim 6, wherein the thinner, the disinfectant, the povidone iodine, the dilute glutaral and the peroxyacetic acid are mixed together in the volume ratio of 120:0.2:0.2:0.2:0.2 to prepare the additive reagent;

the basic medicament is prepared from the following raw materials in parts by weight: 9-12 parts of the lightyellow sophora root, 9-12 parts of the glabrous greenbrier rhizome, 9-12 parts of the bark of Chinese corktree, 9-12 parts of the raw sessile stemona root, 9-12 parts of the alumen, 9-12 parts of the coptis root, 9-12 parts of the cortex dictamni, 9-12 parts of the chinaberry bark and root-bark, 6-8 parts of the pangolin scales, 3-4 parts of the amber, 9-12 parts of the eucommia bark, 9-12 parts of the tree peony bark, 9-12 parts of the clematis root, 5-7 parts of the common cnidium fruit, 9-12 parts of the Chinese angelica, 20-25 parts of the licorice root, 9-12 parts of the common macrocarpium fruit, 30-35 pails of the barbary wolfberry fruit, 9-12 parts of the medicinal indianmulberry root, 9-12 parts of the cherokee rose fruit, 9-12 parts of the chinaroot greenbrier rhizome, 5-7 parts of the akebia fruit, 9-12 parts of the milkvetch root, 9-12 parts of the Japanese climbing fern spore, 9-12 parts of the asiatic pennywort herb, 9-12 parts of the mulberry leaf and 5-6 parts of the frankincense, which are soaked in 5,000-7,000 parts of the liquor with the alcoholic strength of 30-60% (V/V); and 0.5-0.7 part of the additive reagent is added into the basic medicament.

8. The preparation method of the medicine for treatment or adjuvant treatment of the acquired immunodeficiency syndrome according to claim 6, wherein the thinner, the disinfectant, the povidone iodine, the dilute glutaral and the peroxyacetic acid are mixed together in the volume ratio of 120:0.2:0.2:0.2:0.2 to prepare the additive reagent;

the basic medicament is prepared from the following raw materials in parts by weight: 9-12 parts of the lightyellow sophora root, 9-12 parts of the glabrous greenbrier rhizome, 9-12 parts of the bark of Chinese corktree, 9-12 parts of the raw sessile stemona root, 9-12 parts of the alumen, 9-12 parts of the coptis root, 9-12 parts of the cortex dictamni, 9-12 parts of the chinaberry bark and root-bark, 6-8 parts of pangolin scales, 3-4 parts of the amber, 9-12 parts of the eucommia bark, 9-12 parts of the tree peony bark, 9-12 parts of the clematis root, 5-7 parts of the common cnidium fruit, 9-12 parts of the Chinese angelica, 20-25 parts of the licorice root, 9-12 parts of the common macrocarpium fruit, 30-35 parts of the barbary wolfberry fruit, 9-12 parts of the medicinal indianmulberry root, 9-12 parts of the cherokee rose fruit, 9-12 parts of the chinaroot greenbrier rhizome, 5-7 parts of the akebia fruit, 9-12 parts of the milkvetch root, 9-12 parts of the Japanese climbing fern spore, 9-12 parts of the asiatic pennywort herb, 9-12 parts of the mulberry leaf and 5-6 parts of the frankincense, which are soaked in 5,000-7,000 parts of the liquor with the alcoholic strength of 30-60% (V/V); and 0.5-0.7 part of the additive reagent is added into the basic medicament, and then 250-300 parts of red date and 400-500 parts of hesperidium are added into the basic medicament.

9. A method of treatment or adjuvant treatment of acquired immunodeficiency syndrome comprising administration of the medicine of claim 1 by a method selected from the group consisting of: an oral administration method, an external pasting method, an air-permeable external pasting method and a smearing method;

wherein the oral administration method comprises a step of the patient drinking the medicine directly, or taking the medicine by adding into drinking water and foods;

wherein the external pasting method comprises a step of pouring the medicine on a gauze, then pasting the gauze on a diseased part, and then covering the gauze with a plastic film by pasting and fixing the gauze on the diseased part;

wherein the air-permeable external pasting method comprises a step of pouring the medicine on a gauze, and then pasting the gauze on the diseased part and fixing the gauze on the diseased part; and wherein the smearing method comprises a step of smearing the diseased part with wood lock medicated oil or safflower oil at first, and then smearing with the medicine.

* * * * *